(12) United States Patent (10) Patent No.: US 8,754,380 B2
Omura (45) Date of Patent: Jun. 17, 2014

(54) RADIOGRAPHIC IMAGING APPARATUS AND CONTROL METHOD THEREFOR

(75) Inventor: Satoru Omura, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 361 days.

(21) Appl. No.: 12/852,016

(22) Filed: Aug. 6, 2010

(65) Prior Publication Data

US 2011/0049378 A1 Mar. 3, 2011

(30) Foreign Application Priority Data

Aug. 31, 2009 (JP) ................................. 2009-201089

(51) Int. Cl.
*G01T 1/24* (2006.01)
(52) U.S. Cl.
USPC ............... 250/370.15; 250/336.1; 250/370.01
(58) Field of Classification Search
USPC ............... 250/336.1, 370.01, 370.15
See application file for complete search history.

(56) References Cited

U.S. PATENT DOCUMENTS

| 5,567,944 | A | * | 10/1996 | Rohe et al. | ............... | 250/370.09 |
| 7,889,843 | B2 | | 2/2011 | Watanabe | ..................... | 378/116 |
| 2008/0054182 | A1 | * | 3/2008 | Yokoyama et al. | ...... | 250/370.09 |
| 2010/0102239 | A1 | * | 4/2010 | Hahn et al. | ............... | 250/363.05 |

FOREIGN PATENT DOCUMENTS

| JP | 2008-036399 | 2/2008 |
| JP | 2009-028234 | 2/2009 |
| JP | 2009-178443 | 8/2009 |

OTHER PUBLICATIONS

English Translation of Takeshi, et al., JP 2009-0282234A.*

* cited by examiner

*Primary Examiner* — Matthew Mikels
(74) *Attorney, Agent, or Firm* — Fitzpatrick, Cella, Harper & Scinto

(57) ABSTRACT

A radiographic imaging apparatus comprising: a radiation detector configured to be detachable with respect to a patient platform and detect radiation transmitted through an object in one of a moving image capturing mode and a still image capturing mode; a detection unit configured to detect a shift timing of an image capturing mode; a cooling mechanism configured to cool the radiation detector in one of a first cooling mode and a second cooling mode having a higher cooling capacity than the first cooling mode; and a control unit configured to switch the cooling modes of the cooling mechanism based on detection by the detection unit.

15 Claims, 4 Drawing Sheets

RADIOGRAPHIC IMAGING APPARATUS AND CONTROL METHOD THEREFOR

BACKGROUND OF THE INVENTION

1. Field of the Invention

The present invention relates to a radiographic imaging apparatus and a control method for the apparatus.

2. Description of the Related Art

Digital radiographic imaging apparatuses using DR (Digital Radiography) are mainly used for still image capturing. Such a digital radiographic imaging apparatus is smaller in size and lighter in weight than an I.I. TV imaging system having a similar imaging area, and hence is used for moving image capturing. Therefore, the market is demanding a radiation detector that can perform both still image capturing using an electronic cassette (using DR) and moving image capturing that is performed while the cassette is placed on a table or platform.

An electronic cassette using DR requires higher power consumption when performing continuous shooting or moving image capturing than when performing still image capturing. For this reason, when this cassette is placed on a support base such as a table or platform, a cooling mechanism is placed on the support base. There is known a technique of controlling the driving of the cooling mechanism based on the detection of a temperature inside the cassette (Japanese Patent Laid-Open No. 2009-28234).

When an electronic cassette is used while being placed on a support base, the electronic cassette does not come into contact with a patient. For this reason, there is no need to satisfy the exterior temperature requirement for the electronic cassette. However, when the electronic cassette is removed from the support base, the electronic cassette needs to satisfy the exterior temperature requirement.

In general, as a cooling mechanism, a fan is often used because of its low cost and simple arrangement. When, however, cooling is always performed by using the fan, motor sound noise and power consumption are uselessly large, resulting in inefficiency. This gives an object a feeling of discomfort. According to the technique disclosed in Japanese Patent Laid-Open No. 2009-28234 described above, for example, since only a temperature detection result in a cassette is used as a control criterion for cooling, cooling is always performed to satisfy the exterior temperature requirement for the cassette regardless of whether moving image capturing or still image capturing is performed. For this reason, for example, unnecessary cooling is performed even at the time of still image capturing.

SUMMARY OF THE INVENTION

The present invention provides a technique of switching the cooling modes of an electronic cassette depending on whether moving image capturing or still image capturing is performed.

According to a first aspect of the present invention there is provided a radiographic imaging apparatus comprising: a radiation detector configured to be detachable with respect to a patient platform and detect radiation transmitted through an object in one of a moving image capturing mode and a still image capturing mode; a detection unit configured to detect a shift timing of an image capturing mode in the radiation detector; a cooling mechanism configured to cool the radiation detector in one of a first cooling mode and a second cooling mode having a higher cooling capacity than the first cooling mode; and a control unit configured to switch the cooling modes of the cooling mechanism based on detection by the detection unit.

According to a second aspect of the present invention there is provided a control method for a radiographic imaging apparatus, the method comprising: causing a radiation detector which is detachable with respect to a patient platform to detect radiation transmitted through an object in one of a moving image capturing mode and a still image capturing mode; causing a detection unit to detect a shift timing of an image capturing mode in the radiation detector; causing a cooling mechanism to cool the radiation detector in one of a first cooling mode and a second cooling mode having a higher cooling capacity than the first cooling mode; and causing a control unit to switch the cooling modes of the cooling mechanism based on detection by the detection unit.

Further features of the present invention will be apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

The following embodiments will exemplify a case in which X-rays are used as radiation. However, radiation is not limited to X-rays but may be electromagnetic waves, α-rays, β-rays, or γ-rays.

(First Embodiment)

Figure 1A:
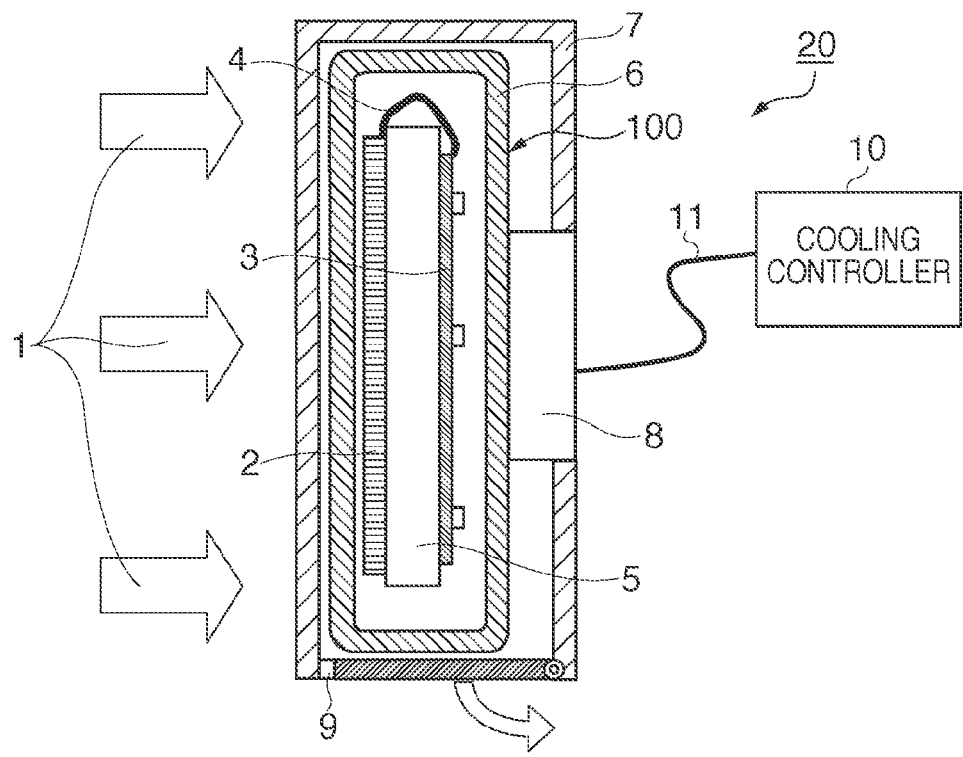
FIGS. 1A and 1B are views showing an example of the arrangement of a radiographic imaging apparatus according to an embodiment of the present invention.
Figure 1B:
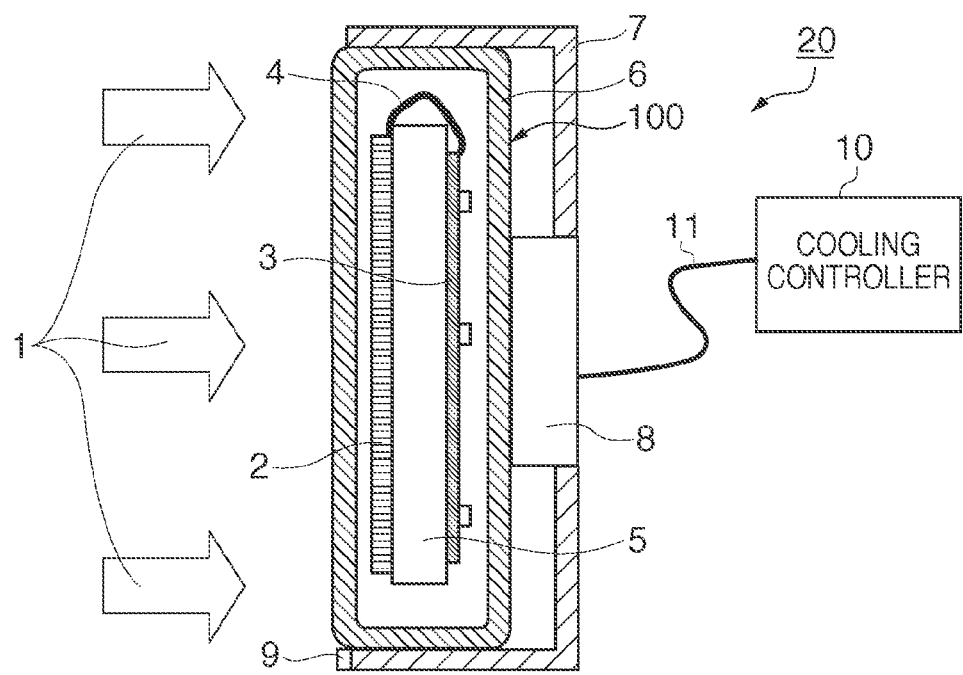

FIGS. 1A and 1B show an example of the arrangement of a radiographic imaging apparatus according to an embodiment of the present invention.

A radiographic imaging apparatus 20 includes a cooling controller 10 and a patient platform 7. The cooling controller 10 is communicatively connected to the patient platform 7 via a cable 11.

The patient platform 7 is a base to support a patient, in which electronic cassette (to be sometimes simply referred to as a cassette or radiation detector hereinafter) 100 is detachably mounted. As the patient platform 7, for example, a decubitus table, standing-position platform, universal platform, or the like is used.

In this case, the electronic cassette 100 detects radiation transmitted through an object (an object to be examined in this embodiment) and acquires a radiation image based on the object. The electronic cassette 100 is used while being mounted in the patient platform 7 and is portably used singly. In this embodiment, when the electronic cassette 100 is portably used, still image capturing (a still image capturing mode) is performed, whereas when the electronic cassette 100 is used while being mounted in the platform, moving image capturing (a moving image capturing mode) is performed. In the case shown in FIG. 1A, a side surface of the patient platform 7 opens and closes, and the electronic cassette 100 is mounted in the patient platform 7 by being inserted through the side surface. In the case shown in FIG. 1B, the surface on the radiation incident direction 1 side is open, and the electronic cassette 100 is mounted in the patient platform 7 by being inserted through this open surface. Note that the still image capturing mode is a mode of performing one capturing operation for each radiation emission, whereas the moving image capturing mode is a mode of continuously performing capturing operation for each radiation emission.

The patient platform 7 is provided with a detection unit 9. The detection unit 9 detects the shift timing of a capturing mode (the moving image capturing mode or still image capturing mode). In the case shown in FIG. 1A, the detection unit 9 detects that the side surface of the patient platform 7 has opened. With this operation, the detection unit 9 detects the shift timing of a capturing mode. Note that the detection unit 9 may be placed on a portion where it comes into contact with the operator when the electronic cassette 100 is detached/attached, for example, a handle portion. In this case, the side surface of the patient platform 7 is preferably open, through which the electronic cassette 100 is detached/attached. In the case shown in FIG. 1B, the detection unit 9 is placed on an end portion on the radiation incident direction 1 side of the patient platform 7. In this case, the detection unit 9 is implemented by an infrared sensor or the like and detects that the object has reached a predetermined range. This detects the shift timing of a capturing mode.

The electronic cassette 100 includes, in an exterior 6 thereof, an electronic substrate 3, a support base 5, and a radiation detection unit 2. Reference numeral 1 denotes the incident direction of radiation. The radiation detection unit 2 detects the radiation transmitted through an object. The electronic substrate 3 receives the signal detected by the radiation detection unit 2 via an electric signal line 4, and processes the signal. The support base 5 supports the radiation detection unit 2.

The patient platform 7 is provided with a cooling mechanism 8 to cool an electronic cassette exterior 6. The cooling mechanism 8 according to this embodiment operates in two stages including a normal heat dissipation mode (first cooling mode) and a high heat dissipation mode (second cooling mode). The high heat dissipation mode is a mode with a higher cooling capacity than that of the normal heat dissipation mode. The cooling mechanism 8 can be implemented by any mechanism, for example, a contact type or non-contact type cooling mechanism such as a Peltier device, a fan, or water cooling mechanism. The disposition place of the cooling mechanism 8 can be any surface excluding the surface on the radiation incident direction 1 side of the patient platform 7. In addition, the cooling mechanism 8 may be disposed in the electronic cassette. Note that the cooling mechanism 8 in this embodiment will be described by exemplifying a case in which the cooling mechanism to be used can adjust its output in two or more stages. However, the present invention is not limited to this. For example, it is possible to dispose a plurality of cooling mechanisms 8 and selectively drive them. In this case, for example, in the normal heat dissipation mode, one cooling mechanism is driven. In the high heat dissipation mode, two or more cooling mechanisms are driven.

The cooling controller 10 controls the driving of the cooling mechanism 8. The cooling controller 10 may be disposed in the patient platform 7. Note that the cooling controller 10 includes one or a plurality of computers. The computer includes, for example, a main control unit such as a CPU and storage units such as a ROM (Read Only Memory) and RAM (Random Access Memory). The computer may also include a communication unit such as a network card and input/output units such as a keyboard and a display or a touch panel. Note that these components are connected to each other via a bus or the like, and the main control unit executes programs stored in the storage unit to control the components.

Figure 2:
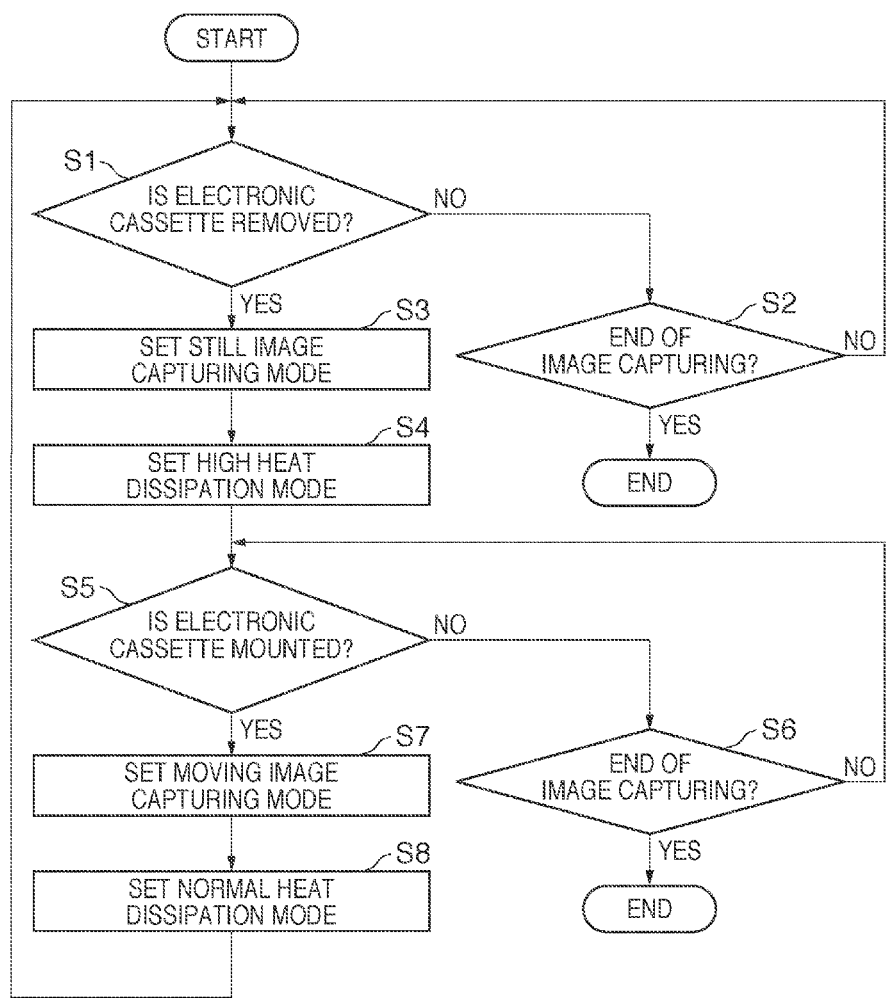
FIG. 2 is a flowchart showing an example of the capturing operation of the radiographic imaging apparatus shown in FIG. 1A.

FIG. 2 is a flowchart showing an example of the capturing operation of the radiographic imaging apparatus 20 shown in FIG. 1A. For the sake of descriptive convenience, assume that image capturing has started while an electronic cassette is mounted in the patient platform 7.

The radiographic imaging apparatus 20 captures a radiation image in the moving image capturing mode because the electronic cassette 100 is mounted in the patient platform 7. At this time, the cooling mechanism 8 operates in the normal heat dissipation mode and cools the electronic cassette 100. This state continues until the detection unit 9 detects that the electronic cassette 100 has been removed from the patient platform 7 or the user has issued an instruction to end image capturing (NO in step S2 after NO in step S1).

If the user issues an instruction to end image capturing (YES in step S2), the radiographic imaging apparatus 20 terminates this processing. If the detection unit 9 detects the removal of the electronic cassette 100 from the patient platform 7 (that is, the shift timing of the image capturing mode) (YES in step S1), the radiographic imaging apparatus 20 notifies the cooling controller 10 of the corresponding information. The radiographic imaging apparatus 20 shifts the image capturing mode to the still image capturing mode (S3).

In this case, the cooling mechanism 8 starts operating in the high heat dissipation mode based on an instruction from the cooling controller 10 (S4). This state continues until the detection unit 9 detects that the electronic cassette 100 has been mounted in the patient platform 7 or the user has issued an instruction to end image capturing (NO in step S6 after NO in step S5). Note that, as described above, in the still image capturing mode, the radiographic imaging apparatus 20 performs image capturing while the object is in contact with the electronic cassette exterior 6.

If the user issues an instruction to end image capturing (YES in step S6), the radiographic imaging apparatus 20 terminates this processing. If the detection unit 9 detects that the patient platform 7 has been mounted in the electronic cassette 100 (YES in step S5), the radiographic imaging apparatus 20 notifies the cooling controller 10 of the corresponding information, and shifts the image capturing mode to the moving image capturing mode (S7). The cooling mechanism 8 starts operating in the normal heat dissipation mode based on an instruction from the cooling controller 10 (S8). The radiographic imaging apparatus 20 then returns to the processing in step S1 again.

Figure 3:
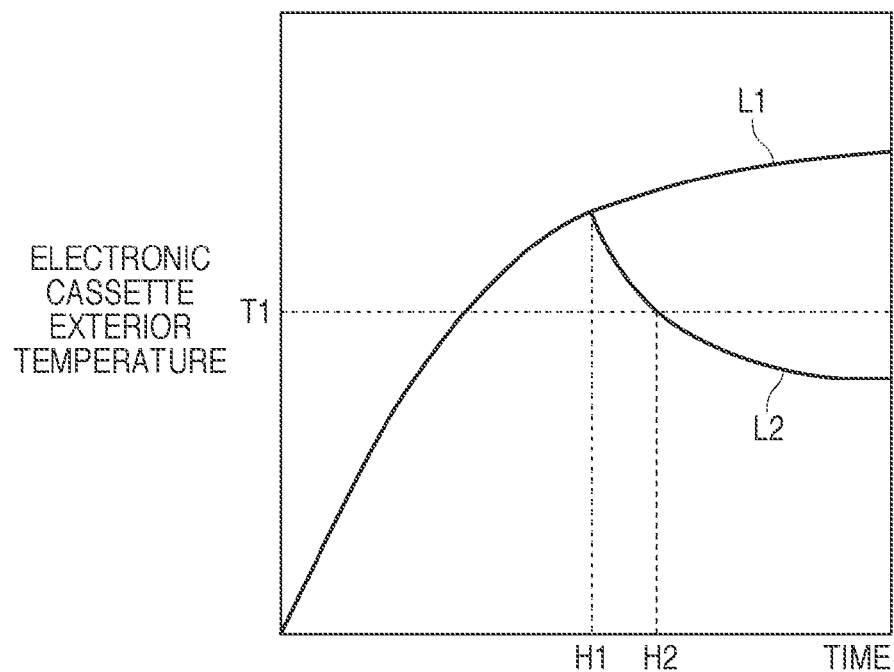
FIG. 3 is a graph showing an example of an outline of the temperature distribution of an electronic cassette exterior 6.

FIG. 3 shows an example of an outline of the temperature distribution of the electronic cassette exterior 6.

Reference symbol T1 denotes an electronic cassette exterior temperature specified value. When the temperature rises above this specified value, it is necessary to prevent the electronic cassette from contacting the object. Reference numeral H1 denotes a shift timing from the moving image capturing mode to the still image capturing mode; H2, the timing at which the electronic cassette 100 has been actually removed from the patient platform 7; L1, a relationship between the time and the electronic cassette exterior temperature when the moving image capturing mode continues; and L2, a relationship between the time and the electronic cassette exterior temperature when the normal heat dissipation mode shifts to the high heat dissipation mode at the timing H1.

As shown in FIG. 3, when the electronic cassette 100 is removed from the patient platform 7, since the cooling mechanism 8 operates in the high heat dissipation mode, it is possible to satisfy the temperature requirement for the electronic cassette exterior 6.

As described above, according to the first embodiment, the cooling mode of the electronic cassette is switched in accordance with an image capturing mode. More specifically, when the electronic cassette mounted in the patient platform 7 is to be used, the normal heat dissipation mode is activated. When the electronic cassette is to be portably used, the high heat dissipation mode is activated. This can properly perform cooling while suppressing power consumption, and hence can improve the cooling efficiency.

(Second Embodiment)

Figure 4:
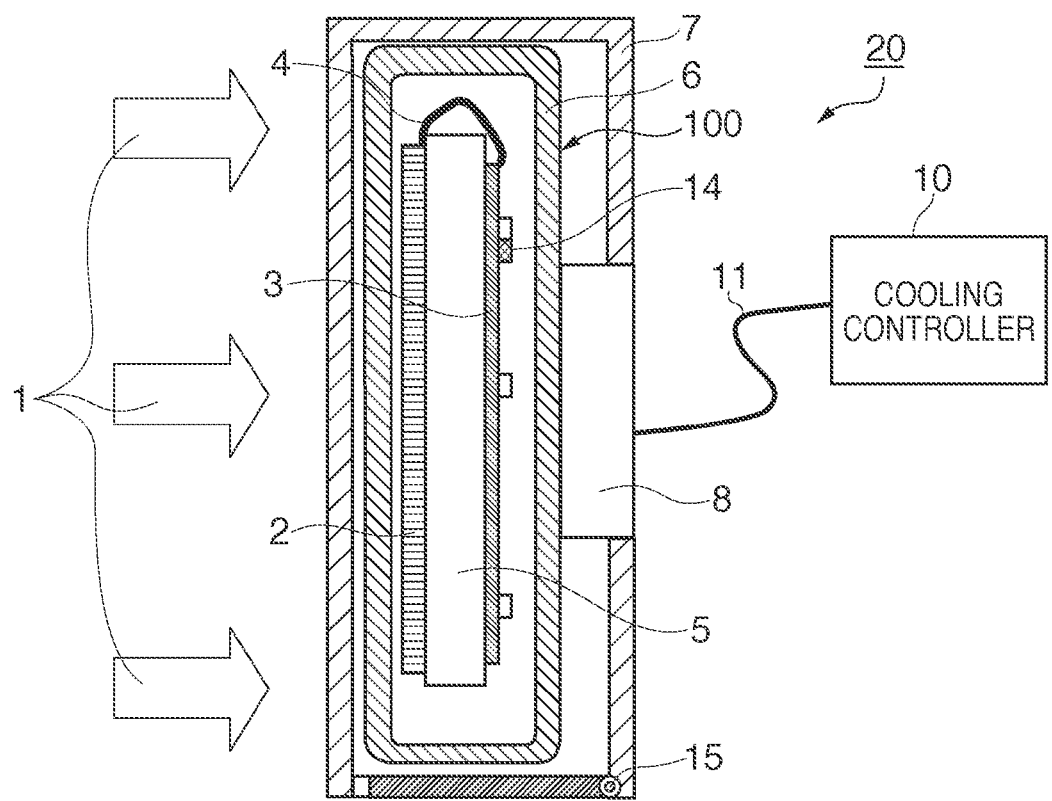
FIG. 4 is a view showing an example of the arrangement of a radiographic imaging apparatus according to the second examination.

FIG. 4 is a graph showing an example of the arrangement of a radiographic imaging apparatus 20 according to the second embodiment. The same reference numerals as in FIG. 1A explaining the first embodiment denote the same parts in FIG. 4, and a description of the parts may be omitted. Note that a description of the arrangement described with reference to FIG. 1B will be omitted.

The radiographic imaging apparatus 20 according to the second embodiment is newly provided with a temperature sensor 14 and a lock mechanism 15.

The temperature sensor 14 detects the surface temperature of an electronic cassette exterior 6 in particular. Although the temperature sensor 14 according to the second embodiment is placed on an electronic substrate 3, since it is possible to calculate an electronic cassette exterior temperature from the temperature distribution of the electronic cassette based on prior measurement, the sensor may be placed on another place. For example, the sensor may be placed on the surface of an electronic cassette 100 or at any position inside the cassette as long as the sensor does not interfere with image capturing.

The lock mechanism 15 locks the opening/closing door of a patient platform 7 to inhibit the removal of the electronic cassette 100. More specifically, the lock mechanism 15 inhibits the opening/closing surface of the patient platform 7 from opening. Note that, for the case of the patient platform (the opening/closing surface is the open surface) corresponding to FIG. 1B described in the first embodiment, a rotatable projection on which an electronic cassette is caught may be placed as a lock mechanism in the patient platform. Inhibiting the rotation of the projection will inhibit the removal of the electronic cassette 100.

In addition to the operation in the first embodiment, a cooling controller 10 according to the second embodiment performs the operation of receiving a signal from the temperature sensor 14 and controlling the lock mechanism 15 based on the signal.

Figure 5:
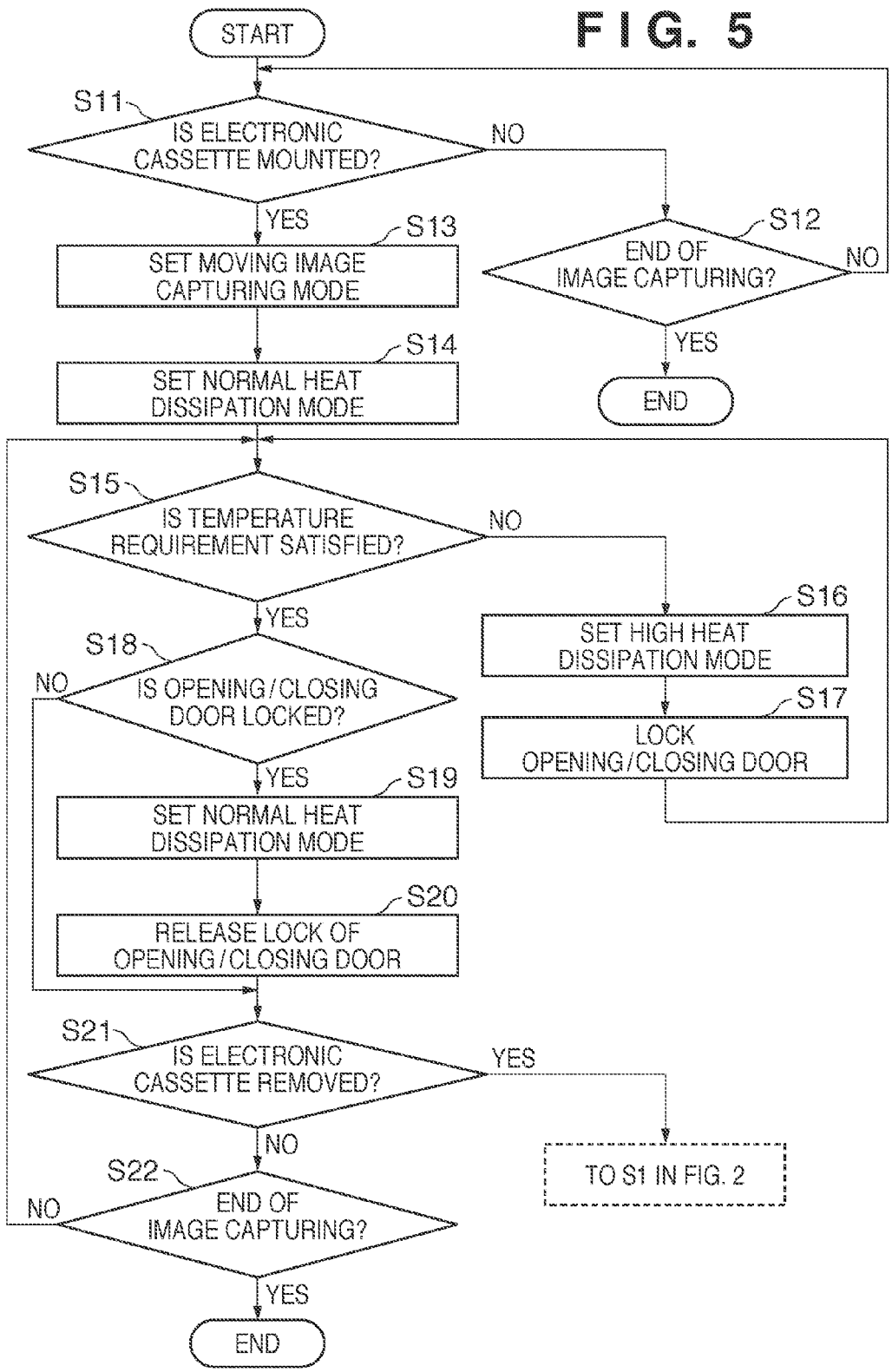
FIG. 5 is a flowchart showing an example of the capturing operation of the radiographic imaging apparatus according to the second embodiment.

An example of the image capturing operation of the radiographic imaging apparatus 20 according to the second embodiment will be described next with reference to FIG. 5. Since the processing to be performed when the electronic cassette 100 is portably used (while not being mounted in the patient platform 7) differs from that in the first embodiment, the processing to be performed when the electronic cassette 100 is mounted in the patient platform 7 will be described below.

When the patient platform 7 is mounted in the electronic cassette 100 (YES in step S11), the radiographic imaging apparatus 20 starts image capturing in the moving image capturing mode (S13). At this time, a cooling mechanism 8 operates in the normal heat dissipation mode to cool the electronic cassette 100 (S14). While the electronic cassette 100 is mounted in the patient platform 7, the temperature sensor 14 notifies the cooling controller 10 of the surface temperature detected from the electronic cassette exterior 6, as needed.

While the electronic cassette 100 is mounted in the patient platform 7, the cooling controller 10 determines, based on the temperature notified from the temperature sensor 14, whether the temperature of the electronic cassette exterior 6 satisfies a temperature requirement. That is, the cooling controller 10 determines whether the temperature of the electronic cassette exterior 6 exceeds a predetermined temperature (does not satisfy the temperature requirement) or is lower or equal to than the predetermined temperature (satisfies the temperature requirement).

Upon determining that the temperature requirement is not satisfied (NO in step S15), the cooling controller 10 issues an instruction to operate in the high heat dissipation mode to the cooling mechanism 8, and also issues an instruction to lock to the lock mechanism 15. With this operation, the cooling mechanism 8 starts operating in the high heat dissipation mode (S16), and the lock mechanism 15 locks the opening/closing door (S17).

Upon determining in step S15 that the temperature requirement is satisfied (YES in step S15), the cooling controller 10 determines whether the lock is being activated. If the lock is being activated (YES in step S18), the cooling controller 10 issues an instruction to operate in the normal heat dissipation mode to the cooling mechanism 8, and also issues an instruction to release the lock to the lock mechanism 15. With this operation, the cooling mechanism 8 starts operating in the normal heat dissipation mode (S19), and the lock mechanism 15 releases the lock of the opening/closing door (S20). Thereafter, the radiographic imaging apparatus 20 repeatedly executes the processing in steps S15 to S22 until the detection unit 9 detects that the electronic cassette 100 has been removed from the patient platform 7 or the user has issued an instruction to end image capturing (NO in step S22 after NO in step S21).

As described above, according to the second embodiment, even if the temperature of the electronic cassette rises to an unexpectedly high temperature due to long-time moving image capturing operation, a duty error, or the like, it is possible to satisfy the temperature requirement for the electronic cassette exterior 6. This can improve the safety.

In the second embodiment described above, the radiographic imaging apparatus 20 is provided with the temperature sensor 14. However, it is possible to omit the temperature sensor 14. In this case, the cooling controller 10 acquires an imaging condition history externally (for example, from an RIS (Radiology Information System)) and calculates a necessary cooling time (the time required for dropping the temperature of the electronic cassette to the specified temperature or lower) based on the acquired history and the temperature characteristics of the electronic cassette 100. When changing the image capturing mode (shifting from the moving image capturing mode to the still image capturing mode), the cooling controller 10 activates the lock during the cooling time, and releases the lock after the lapse of the cooling time. A supplementary description will be given with reference to FIG. 5. In the processing in step S16, the cooling controller 10 calculates a necessary cooling time (the difference between H1 and H2 in this case) based on the imaging condition history and the temperature characteristics of the electronic cassette 100. The cooling controller 10 then causes the cooling mechanism 8 to operate in the high heat dissipation mode and activates the lock during the calculated cooling time. With this operation, when the electronic cassette 100 is removed from the patient platform 7, the temperature of the electronic cassette exterior drops to satisfy the temperature requirement.

The typical embodiments of the present invention have been described above. However, the present invention is not limited to the embodiments described above and shown in the accompanying drawings, and can be modified and executed as needed within the spirit and scope of the invention.

For example, although the first and second embodiments have not particularly referred to any arrangement using an RIS (Radiology Information System), it is possible to use information from the RIS. For example, the cooling controller 10 may acquire information such as imaging conditions for an examination to be made from the RIS, calculate, based on the information, the time at which the moving image capturing mode shifts to the still image capturing mode, and control the driving of the cooling mechanism 8. This can eliminate the necessity of the temperature sensor and hence can achieve cost reduction. In addition, detecting a shift from the moving image capturing mode to the still image capturing mode in advance makes it possible to start cooling for the still image capturing mode in advance. This makes it possible to perform heat dissipation more efficiently.

In addition, the present invention can take embodiments as a system, apparatus, method, program, storage medium, and the like. The present invention can be applied to a system including a plurality of devices, or to an apparatus including a single device.

According to the present invention, it is possible to switch the cooling modes of an electronic cassette depending on whether moving image capturing or still image capturing is performed.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-201089 filed on Aug. 31, 2009, which is hereby incorporated by reference herein in its entirety.

What is claimed is:

1. A radiographic imaging apparatus comprising:
a radiation detector detachable with respect to a base member and for detecting radiation transmitted through an object in one of plural image capturing modes, said plural image capturing modes including a moving image capturing mode and a still image capturing mode;
a detection unit configured to detect a shift from one of said plural image capturing modes to another mode of said plural image capturing modes in said radiation detector;
a cooling mechanism configured to cool said radiation detector in one of a first cooling mode and a second cooling mode having a higher cooling capacity than the first cooling mode; and
a control unit configured to switch the cooling modes of said cooling mechanism in response to detection by said detection unit,
wherein said radiation detector is operable in the moving image capturing mode in a case in which said radiation detector is mounted in the base member and is configured to operate in the still image capturing mode in a case in which said radiation detector is removed from the base member, and
wherein said control unit is configured to cause said cooling mechanism to operate in the second cooling mode in response to said detection unit detecting a shift from the moving image capturing mode to the still image capturing mode, and is configured to cause said cooling mechanism to operate in the first cooling mode in response to said detection unit detecting a shift from the still image capturing mode to the moving image capturing mode.

2. The apparatus according to claim 1, wherein said detection unit is configured to detect a shift of the image capturing mode based on whether said radiation detector is mounted in or removed from said base member.

3. The apparatus according to claim 1, wherein said detection unit is configured to detect a shift of the image capturing mode based on information including an externally acquired imaging condition.

4. The apparatus according to claim 1, wherein said detection unit is configured to detect a shift of the image capturing mode based on an approach of said radiation detector to a predetermined range of the object.

5. The apparatus according to claim 1, further comprising
a temperature sensor configured to detect a surface temperature of said radiation detector, and
a lock mechanism configured to activate a lock to inhibit said radiation detector from being removed from said base member,
wherein said control unit, in the case than said radiation detector is mounted in said base member, is configured to cause said lock mechanism to activate the lock while causing said cooling mechanism to operate in the second cooling mode when a temperature from said temperature sensor exceeds a predetermined temperature, and is configured to cause said lock mechanism to release the lock while causing said cooling mechanism to operate in the first cooling mode when a temperature from said temperature sensor is lower than or equal to said predetermined temperature.

6. The apparatus according to claim 1, further comprising a lock mechanism configured to activate a lock to inhibit said radiation detector from being removed from said base member,
wherein said control unit is configured to cause said lock mechanism to active the lock during a time which is calculated based on an externally acquired imaging condition history and required for dropping a temperature of said cooling mechanism to lower than or equal to a predetermined temperature, when said radiation detector is mounted in said base member and said detection unit detects a shift from the moving image capturing mode to the still image capturing mode.

7. A control method for a radiographic imaging apparatus, the method comprising:
  causing a radiation detector which is detachable with respect to a base member to detect radiation transmitted through an object in one of plural image capturing modes, said plural image capturing modes including a moving image capturing mode and a still image capturing mode;
  causing a detection unit to detect a shift from one of said plural image capturing modes to another mode of said plural image capturing modes in the radiation detector;
  causing a cooling mechanism to cool the radiation detector in one of a first cooling mode and a second cooling mode having a higher cooling capacity than the first cooling mode; and
  causing a control unit to switch the cooling modes of the cooling mechanism in response to detection by the detection unit,
  wherein the radiation detector is operable in the moving image capturing mode in a case in which the radiation detector is mounted in the base member and is configured to operate in the still image capturing mode in a case in which the radiation detector is removed from the base member, and
  wherein the control unit is configured to cause the cooling mechanism to operate in the second cooling mode in response to the detection unit detecting a shift from the moving image capturing mode to the still image capturing mode, and is configured to cause the cooling mechanism to operate in the first cooling mode in response to the detection unit detecting a shift from the still image capturing mode to the moving image capturing mode.

8. A control apparatus for radiographic imaging, comprising:
  a detection unit configured to detect a shift from one of plural image capturing modes to another mode of said plural image capturing modes in a radiation detector detachable with respect to a support base and for detecting radiation transmitted through an object in one of said plural image capturing modes;
  a control unit configured to control, in response to detection by said detection unit, a cooling mechanism for cooling said radiation detector functioning in a plurality of cooling capacities,
  wherein the radiation detector is operable in the moving image capturing mode in a case in which the radiation detector is mounted in the base member and is configured to operate in the still image capturing mode in a case in which the radiation detector is removed from the base member, and
  wherein said control unit is configured to cause the cooling mechanism to operate in the second cooling mode in response to said detection unit detecting a shift from the moving image capturing mode to the still image capturing mode, and is configured to cause the cooling mechanism to operate in the first cooling mode in response to said detection unit detecting a shift from the still image capturing mode to the moving image capturing mode.

9. The apparatus according to claim 1, wherein said control unit is connectable to said base member via a cable.

10. The apparatus according to claim 1, wherein said detection unit is placed on a handle portion of said radiation detector.

11. The apparatus according to claim 1, wherein said cooling mechanism is one of a plurality of cooling mechanisms and each of said plurality of cooling mechanisms can be selectively driven.

12. A control method for a radiographic imaging apparatus, the method comprising:
  causing a radiation detector which is detachable with respect to a base member to detect radiation transmitted through an object in one of plural image capturing modes, said plural image capturing modes including a moving image capturing mode and a still image capturing mode;
  causing a detection unit to detect a shift from one of said plural image capturing modes to another mode of said plural image capturing modes in the radiation detector;
  causing a cooling mechanism to cool the radiation detector in one of a first cooling mode and a second cooling mode having a higher cooling capacity than the first cooling mode; and
  causing a control unit to switch the cooling modes of the cooling mechanism in response to detection by the detection unit,
  wherein the radiation detector is operable in the moving image capturing mode in a case in which the radiation detector is mounted in the base member and is configured to operates in the still image capturing mode in a case in which the radiation detector is removed from the base member, and the control unit is configured to cause the cooling mechanism to operate in the first cooling mode in response to the detection unit detecting a shift from the still image capturing mode to the moving image capturing mode.

13. A control apparatus for radiographic imaging, comprising:
  a detection unit configured to detect a shift from one of plural image capturing modes to another mode of said plural image capturing modes in a radiation detector detachable with respect to a support base and for detecting radiation transmitted through an object in one of said plural image capturing modes;
  a control unit configured to control, in response to detection by said detection unit, a cooling mechanism for cooling the radiation detector functioning in a plurality of cooling capacities,
  wherein the radiation detector is operable in the moving image capturing mode in a case in which the radiation detector is mounted in the base member and is configured to operate in the still image capturing mode in a case in which the radiation detector is removed from the base member, and
  wherein said control unit is configured to cause the cooling mechanism to operate in the first cooling mode in response to the detection unit detecting a shift from the still image capturing mode to the moving image capturing mode.

14. A non-transitory computer-readable medium storing a computer-executable program for causing a computer to execute the method of claim 12.

15. A non-transitory computer-readable medium storing a computer-executable program for causing a computer to serve as each unit of the control apparatus of claim 13.

* * * * *